US00PP34975P3

(12) United States Plant Patent
Scalzo et al.

(10) Patent No.: US PP34,975 P3
(45) Date of Patent: Feb. 14, 2023

(54) BLUEBERRY PLANT NAMED 'C14-409'

(50) Latin Name: *Vaccinium corymbosum*
Varietal Denomination: 'C14-409'

(71) Applicants: Costa Berry International Pty Ltd, Ravenhall (AU); FLORIDA FOUNDATION SEED PRODUCERS, INC., Marianna, FL (US)

(72) Inventors: Jessica Scalzo, Corindi Beach (AU); James W. Olmstead, Aptos, CA (US)

(73) Assignees: COSTA BERRY INTERNATIONAL PTY LTD, Revenhall (AU); FLORIDA FOUNDATION SEED PRODUCERS, INC., Marianna, FL (US)

( * ) Notice: Subject to any disclaimer, the term of this patent is extended or adjusted under 35 U.S.C. 154(b) by 0 days.

(21) Appl. No.: 17/803,050

(22) Filed: Jan. 26, 2022

(65) Prior Publication Data

US 2022/0248584 P1 Aug. 4, 2022

Related U.S. Application Data

(60) Provisional application No. 63/206,159, filed on Jan. 29, 2021.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

*Primary Examiner* — Susan McCormick Ewoldt
(74) *Attorney, Agent, or Firm* — Baker & McKenzie LLP

(57) ABSTRACT

The new blueberry plant variety 'C14-409' is provided. 'C14-409' is a commercial variety intended for the fresh market. The variety is produced from a cross of unpatented parents 'FL09-315' and 'FL07-285'.

5 Drawing Sheets

Latin name of the genus, and species: Genus—*Vaccinium*. Species—*corymbosum* hybrid.

Variety denomination: The new blueberry plant claimed is of the variety denominated 'C14-409'.

BACKGROUND OF THE INVENTION

The new variety 'C14-409' was selected from a population of seedlings derived from crossing the blueberry varieties known as 'FL09-315' (unpatented seed parent) and the variety known as 'FL07-285' (unpatented pollen parent). The cross was made in 2010 in Florida, USA and the seed was sown and grown in Corindi Beach, New South Wales, Australia. The new variety was selected in 2014 from among plants located on land at Corindi Beach and assigned the breeding code 'C14-409'. Plants of 'C14-409' were propagated by cuttings for further evaluation and resulted to be uniform and stable. The new variety showed distinctive traits such as evergreen, with fruit of good flavor, and good picking scar.

SUMMARY OF THE INVENTION

The new variety 'C14-409' was originated from a cross of 'FL09-315' (unpatented seed parent) and the variety known as 'FL07-285' (unpatented pollen parent) in 2010 in Florida, USA.

The new blueberry variety resulted from seedlings produced in a controlled breeding programme. The cross was made in 2010 in Florida, USA and the seed was sown and grown in Corindi Beach, New South Wales, Australia.

The new variety was selected in 2014 from among plants located on land at Corindi Beach and has since been named 'C14-409'. Since then plants of 'C14-409' were propagated by cuttings for further evaluation and confirmed to be uniform and stable. Asexual reproduction of the new variety 'C14-409' by cutting propagation since 2014 at Corindi Beach, New South Wales, Australia has demonstrated that the new variety reproduces true to type plants.

The new variety was selected in 2014 as a single plant within a population of seedlings resulting from controlled cross of *Vaccinium* varieties. The seedling population was planted in an experimental block in the field at Corindi Beach, New South Wales, Australia and the selection of the new variety took place in the same block. Selection criteria were a combination of very early cropping time, low chilling requirement, medium vigour, non-deciduous type of plant (evergreen), large fruit size, good fruit flavor, and firm fruit. The new variety was subsequently evaluated for six years at the commercial farm at Corindi Beach, New South Wales, Australia.

The following characteristics of the new variety have been repeatedly observed and can be used to distinguish 'C14-409' as a new and distinct variety of *Vaccinium corymbosum* hybrid:

1. Non-deciduous (Evergreen)
2. Very early season crop
1. Low chilling requirement, estimated to be between 0 to 300 hours
2. Large fruit size, average of 3.3 g
3. Strong bloom
4. Small and dry fruit picking scar The new blueberry variety 'C14-409' has maintained its distinguished characteristics throughout successive asexual propagation. The variety has been repeatedly asexually reproduced through softwood cuttings in New South Wales, Australia and the clones are phenotypically identical to the original plant.

BRIEF DESCRIPTION OF THE DRAWINGS

The accompanying photographic illustration shows typical specimens in full color of the foliage and fruit of the new variety 'C14-409'. The colors are as nearly true as is reasonably possible in a color representation of this type.

Figure 1:
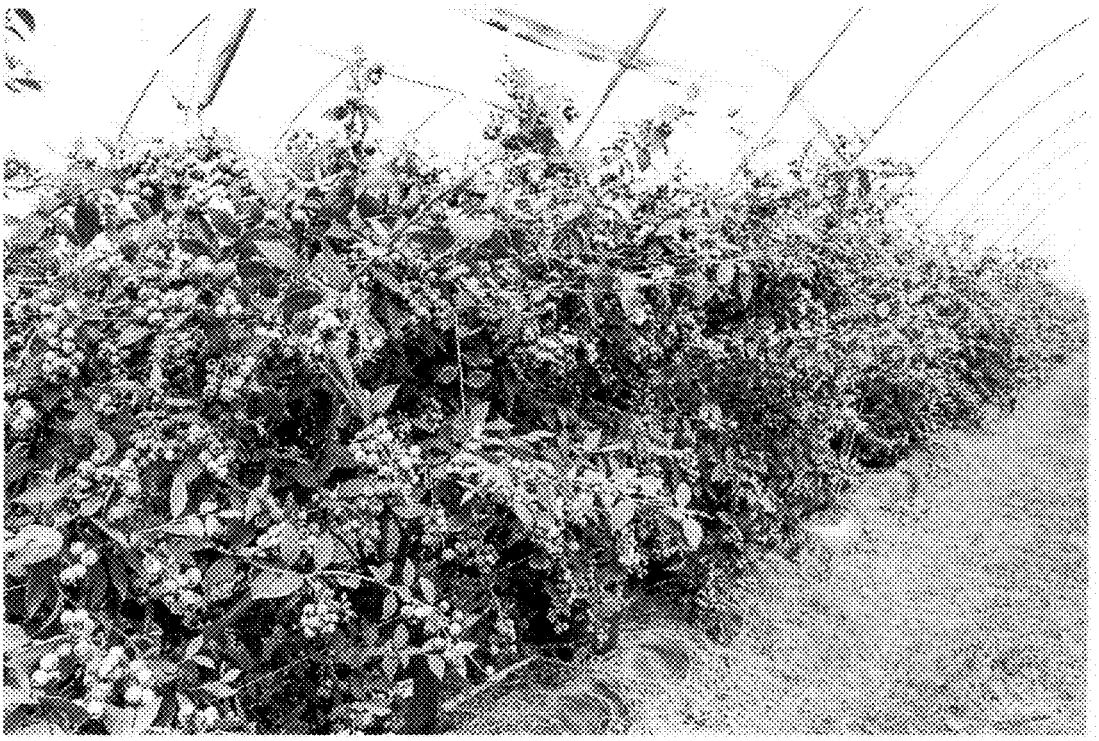
FIG. 1 is a photograph showing two-year-old plants of the new variety 'C14-409'.
Figure 2:
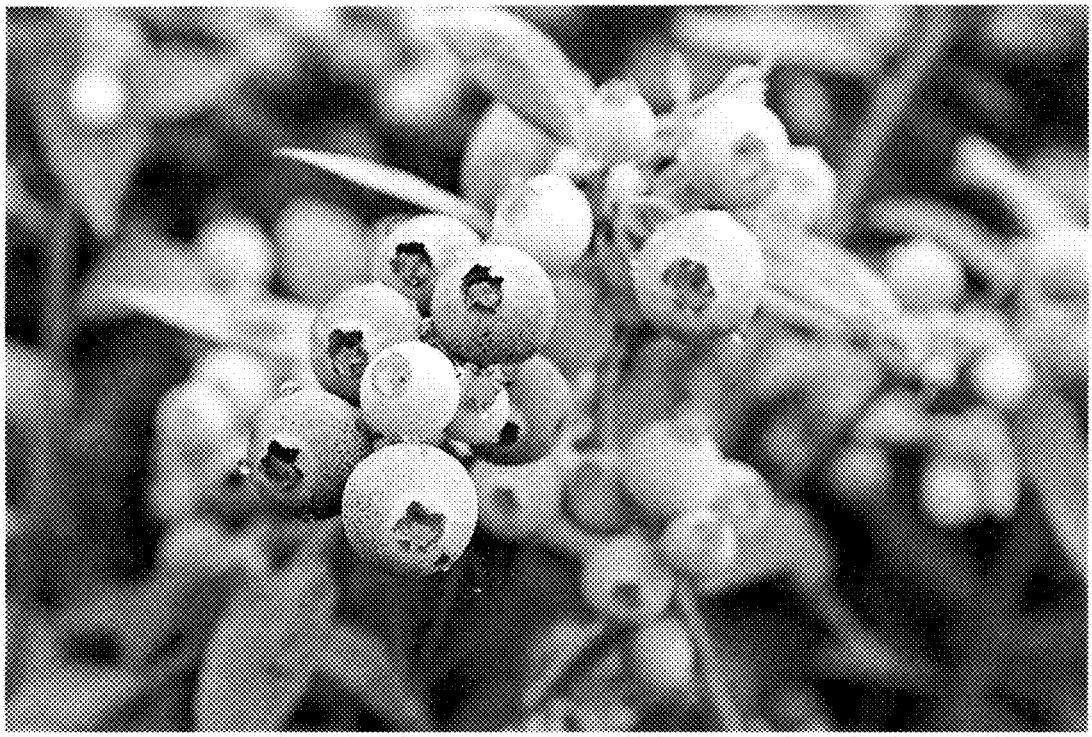
FIG. 2 is a photograph of the typical fruit cluster of the new variety 'C14-409'.
Figure 3:
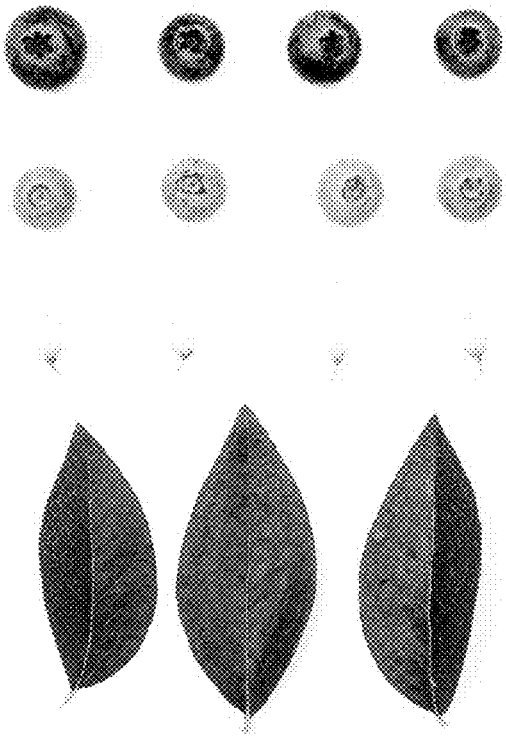
FIG. 3 is a photograph showing the botanical parts (mature fruit, green fruit, flowers and leaves) of the new variety 'C14-409'.
Figure 4:
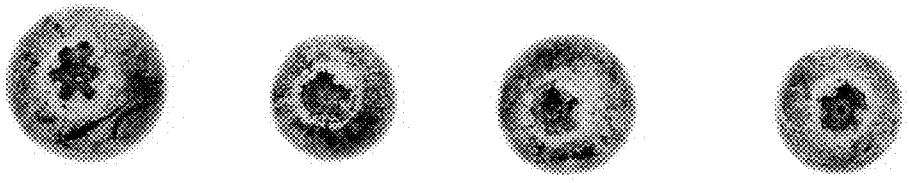
FIG. 4 is a photograph showing the typical fruit calyx of the new variety 'C14-409'.
Figure 5:
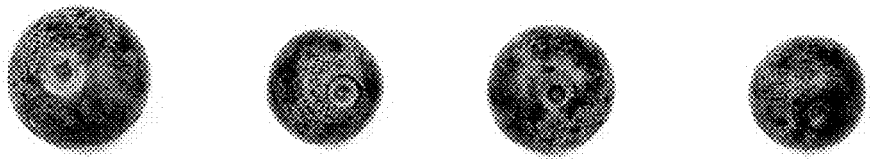
FIG. 5 is a photograph showing the typical pedicel scar of the new variety 'C14-409'.

The colors in the photographs are as close as possible with the photographic and printing technology utilized. The color values cited in the detailed botanical description accurately describe the colors of the new blueberry variety.

DETAILED BOTANICAL DESCRIPTION

The following detailed description sets forth the distinctive characteristics of 'C14-409'. The data which defines these characteristics was collected from asexual reproductions of the original selection. Dimensions, sizes, colors, and other characteristics are approximations and averages set forth as accurately as possible. For all traits data was collected from 3 plant parts across 6 randomly selected plants. For the traits relating to fruits (e.g., fruit weight, firmness, brix, acidity) the data is an average across twenty fruits collected randomly. The plant history was taken on plants approximately 3 years of age, and the descriptions relate to plants grown in the field in Corindi Beach, New South Wales, 2456 Australia. Descriptions of fruit characteristics were made on fruit grown in Corindi Beach, New South Wales, 2456 Australia. Color designations are from the 2007 edition of The Royal Horticultural Society ("R.H.S.") Colour Chart. 'C14-409' has not been observed under all possible environments. The phenotype may vary slightly with different growing environments such as temperature, light, fertility, soil pH, moisture and maturity levels, but without any change in the genotype.

Classification:

*a. Family.*—Ericaceae.
*b. Genus.*—*Vaccinium.*
*c. Species.*—*corymbosum* hybrid.
*d. Common name.*—Blueberry.

Parentage: Female Parent—unpatented selection 'FL09-315'. Male Parent—unpatented selection 'FL07-285'.

Market class: Fresh market.

PLANT

General:

*Parentage.*—FL09-315 x FL07-285.
*Plant height.*—1.6 m.
*Plant width.*—1.5 m.
*Growth habit.*—Semi-upright.
*Growth.*—Medium vigour.
*Mature cane length.*—0.70 m.
*Mature cane width.*—15.14 mm.
*Mature cane color.*—Grey-orange group 165A, and streak of grey-brown group, similar to 199B.
*Bark texture.*—Medium (texture between rough and smooth).
*Fruiting wood in length.*—25 cm.
*Productivity.*—High yield. Average of 6.0 Kg per plant (estimated equivalent production of 13.22 pounds per plant) from 3-year-old plants when growing in 17 L pots at Corindi Beach, NSW. The plants are spaced at 0.7 m apart along the row and 2.5 m between the rows, which gives an estimated plant density of 5700 plants per hectare.
*Cold hardiness.*—Low chill (USDA plant hardiness Zone 4).
*Cold tolerance.*—Low.
*Chilling requirement.*—Low, estimated between 0 and 300 hours.
*Tolerance to disease.*—None assessed.
*Leafing.*—Strong, thick canopy, and plant retains leaves during the winter in low chill environments (zone 4).
*Resistance to disease.*—Resistant to blueberry leaf rust (*Thekopsora minima*).
*Heat tolerance.*—Moderately resistant to heat.
*Twigginess.*—Medium.

FOLIAGE

General:

*Leaf color* (*top side*).—Green group, similar to 139A and 137B.
*Leaf color* (*under side*).—Green group, similar to N138C.
*Leaf arrangement.*—Alternate.
*Leaf shape.*—Elliptic.
*Leaf margins.*—Entire.
*Leaf venation.*—Reticulate.
*Leaf length.*—Medium (average 58.4 mm).
*Leaf width.*—Narrow (average 27.2 mm).
*Leaf length/width ratio.*—2.1.
*Shape of the leaf apex.*—Acute.
*Shape of the leaf base.*—Cuneate.
*Leaf vein color.*—Yellow-green group, similar to 145B.
*Leaf nectaries.*—Absent.
*Pubescence of upper side.*—Absent.
*Pubescence of lower side.*—Absent.
*Cross sectional profile.*—Flat.
*Longitudinal profile.*—Straight.
*Attitude.*—Horizontal.

Petioles:

*Length.*—Average 4.6 mm.
*Width.*—Average 1.5 mm.
*Color.*—Yellow green group, similar to 144D.
*Texture.*—Smooth.

FLOWERS

General:

*Time of beginning of flowering.*—Very early to early season (50% of anthesis estimated to be between the last week of May and the 1$^{st}$ of June, on 3 year old plants, cultivated at Corindi Beach, NSW).
*Flowering interval on one-year old shoot.*—May to mid July.

*Flowering interval on current year shoot*.—May to July.
*Flower shape*.—Urceolate.
*Flower fragrance*.—None perceptible.

Corolla:
*Shape*.—Urceolate.
*Color*.—White group, similar to NN155C.
*Length*.—8.6 mm.
*Width of widest region*.—8.9 mm.
*Aperture width*.—4.5 mm.
*Anthocyanin coloration of corolla*.—Absent or very weak.
*Corolla ridges*.—Present, average of 5.
*Petal width* (*ridge to ridge*).—4.99 mm.
*Protrusion of stigma*.—Present.
*Corolla/petal texture*.—Smooth.

Inflorescence:
*Inflorescence length* (*excluding peduncle*).—Long, 25.6 mm.
*Inflorescence width*.—23.4 mm.
*Flower length* (*excluding pedicel*).—10.3 mm.
*Flower diameter*.—9.1 mm.
*Flower length/width ratio*.—1.13.
*Length of peduncle*.—40.5 mm.
*Surface texture of peduncle*.—Medium (texture between rough and smooth).
*Color of peduncle*.—Base color is yellow-green group, similar to 146D over color is greyed-red group, similar to 182A.
*Length of pedicel*.—13.2 mm.
*Surface texture of pedicel*.—Smooth.
*Color of pedicel*.—Yellow-green group, similar to 146B and 146C.
*Number of flowers per cluster*.—9 on average.
*Flower cluster density*.—Dense.

Calyx (with sepals):
*Diameter*.—6.3 mm.
*Sepal's average number*.—5.
*Shape of the sepal*.—Deltoid.
*Shape apex*.—Acute.
*Margin of the sepal*.—Entire.
*Texture sepal* (*lower side*).—Smooth.
*Texture sepal* (*upper side*).—Smooth.
*Sepal color* (*inside*).—Yellow-green group 144D.
*Sepal color* (*outside*).—Yellow-green group 144C.

Stamen:
*Length*.—7.3 mm.
*Number per flower*.—10.
*Filament color*.—Yellow-green group, similar to 145C and 145D.

Pistil:
*Length*.—11.5 mm.
*Style length* (*including stigma*).—9.5 mm.
*Style color*.—Yellow-green group, similar to N144C.

Anther:
*Length*.—4.9 mm.
*Number per flower*.—10.
*Color*.—Greyed-orange group, similar to 165B.

Pollen:
*Abundance*.—Few.
*Color*.—Yellow group, similar to 4D.
*Self compatibility*.—Yes (this variety shows a high degree of self-compatibility).

FRUIT

General:
*Time of fruit ripening*.—Very early to early, estimated 50% of the fruit ripe on the 10th of August, on 3 year old plants, growing at Corindi Beach, NSW.
*Cluster density*.—Dense (8-11 berries per cluster).
*Unripe fruit color*.—Yellow green group, similar to 144A.
*Ripe berry color*.—Blue group 103A, when bloom is removed.
*Berry surface wax abundance*.—Strong.
*Berry weight*.—On average 3.3 g.
*Berry height from calyx to scar*.—13.8 mm.
*Berry diameter*.—17.3 mm.
*Berry shape*.—Oblate.
*Fruit diameter of calyx basin*.—Medium, on average 6.0 mm.
*Fruit depth of calyx basin*.—Medium to deep.
*Fruit stem scar*.—Small and dry.
*Sweetness when ripe*.—Medium to high (13 Brix).
*Firmness when ripe*.—Firm, 180 g/mm, measured with FirmTech.
*Acidity when ripe*.—Medium to high (0.7%).
*Berry flesh color*.—Yellow-green group, similar to 145D.
*Storage quality*.—Medium, average of 23 days.
*Suitability for mechanical harvesting*.—Not tested.
*Uses*.—Fruit to be hand harvested for fresh market.
*Self fruitfulness*.—Yes.

SEED

General:
*Seed abundance in fruit*.—Abundant, on average 28 seeds per fruit.
*Seed color*.—Greyed orange group, similar to 166B and 166D.
*Seed length*.—1.99 mm.

COMPARISON BETWEEN PARENTAL AND SIMILAR CULTIVARS

Table 1 below provides a comparison between 'C14-409' and similar cultivars:

TABLE 1

Comparison of 'C14-409' with similar cultivars

| Characteristics | 'C14-409' | 'C99-42' (U.S. Plant Pat. No. 20,695P2) | 'Snowchaser' (U.S. Plant Pat. No. 19,503P3) |
|---|---|---|---|
| Plant vigour | Medium | Weak to medium | Medium |
| Plant growth habit | Semi-upright | Semi-upright to intermediate | Semi-upright |
| One year old shoot length of internodes | Short to medium | Very short to short | Short |
| Leaf length | Medium | Short | Long |
| Leaf length (mm) | 58.4 ± 0.6 | 53.10 ± 0.8 | 61.50 ± 0.9 |
| Leaf width | Narrow | Very narrow to narrow | Broad |

TABLE 1-continued

Comparison of 'C14-409' with similar cultivars

| Characteristics | 'C14-409' | 'C99-42' (U.S. Plant Pat. No. 20,695P2) | 'Snowchaser' (U.S. Plant Pat. No. 19,503P3) |
|---|---|---|---|
| Leaf width (mm) | 27.2 ± 1.1 | 22.9 ± 1.3 | 34.3 ± 1.5 |
| Flower bud: anthocyanins coloration | Weak | Very weak | Strong |
| Flower size of corolla | Small | Medium | Medium |
| Flower corolla length (mm) | 8.6 ± 0.2 | 9.7 ± 0.3 | 9.5 ± 0.3 |
| Fruit cluster density | Dense | Sparse | Medium |
| Fruit size | Large | Small to medium | Small to medium |
| Fruit weight (g) | 3.3 ± 0.6 | 1.9 ± 0.39 | 1.7 ± 0.21 |
| Fruit diameter (mm) | 17.3 ± 0.7 | 15.6 ± 0.96 | 15.10 ± 0.97 |
| Fruit intensity of bloom | Strong | Weak to medium | Weak to medium |
| Fruit firmness | Firm | Firm | Soft |

TABLE 1-continued

Comparison of 'C14-409' with similar cultivars

| Characteristics | 'C14-409' | 'C99-42' (U.S. Plant Pat. No. 20,695P2) | 'Snowchaser' (U.S. Plant Pat. No. 19,503P3) |
|---|---|---|---|
| Soluble solid content (%) | 13 | 13.1 | 14.3 |
| Titratable acidity (%) | 0.7 | 0.3 | 0.5 |
| Time of vegetative bud burst | Medium | Early | Early |
| Time of beginning of flowering | Very early to early | Early to medium | Very early to early |
| Time of beginning of fruit ripening | Very early | Early to medium | Very early to early |

The invention claimed is:

1. A new and distinct variety of blueberry plant named 'C14-409', substantially as illustrated and described herein.

* * * * *

C14-409

C14-409

C14-409